United States Patent
Björk et al.

(10) Patent No.: US 6,918,310 B2
(45) Date of Patent: Jul. 19, 2005

(54) SAMPLING APPARATUS

(75) Inventors: Lennart Björk, Molndal (SE); Staffan Folestad, Molndal (SE); Mats Johansson, Molndal (SE); Anders Klevensparr, Molndal (SE); Ingela Niklasson Björn, Molndal (SE)

(73) Assignee: AstraZeneca AB, Sodertalje (SE)

( * ) Notice: Subject to any disclaimer, the term of this patent is extended or adjusted under 35 U.S.C. 154(b) by 92 days.

(21) Appl. No.: 10/466,001

(22) PCT Filed: Jan. 29, 2002

(86) PCT No.: PCT/SE02/00153
§ 371 (c)(1),
(2), (4) Date: Jul. 8, 2003

(87) PCT Pub. No.: WO02/061394
PCT Pub. Date: Aug. 2, 2002

(65) Prior Publication Data
US 2004/0050184 A1  Mar. 18, 2004

(30) Foreign Application Priority Data
Jan. 31, 2001 (SE) .............................................. 0100283

(51) Int. Cl.[7] .............................. G01N 1/16; G01N 1/26
(52) U.S. Cl. .................................. 73/863.81; 73/864.81
(58) Field of Search ...................... 73/863.81, 863.82, 73/863.83, 863.84, 863.85, 863.86, 864.81, 863.24, 864.83

(56) References Cited

U.S. PATENT DOCUMENTS

| | | | | |
|---|---|---|---|---|
| 3,722,291 A | * | 3/1973 | Lindberg ................. | 73/863.81 |
| 4,771,642 A | * | 9/1988 | Parth et al. ............... | 73/863.52 |
| 5,296,197 A | * | 3/1994 | Newberg et al. ............ | 422/103 |
| 5,317,932 A | * | 6/1994 | Westlake et al. .......... | 73/864.73 |
| 5,585,576 A | * | 12/1996 | Jaeger ..................... | 73/863.85 |
| 6,178,830 B1 | * | 1/2001 | Freud ...................... | 73/863.51 |
| 6,345,545 B1 | * | 2/2002 | Linker et al. ............ | 73/863.23 |
| 6,516,677 B1 | * | 2/2003 | Suter ....................... | 73/863.85 |

FOREIGN PATENT DOCUMENTS

| | | | |
|---|---|---|---|
| DE | 3444013 | 7/1985 | |
| GB | 2150917 | 7/1985 | |
| WO | 9323731 | 11/1993 | |
| WO | 9932872 | 7/1999 | |
| WO | WO 99/32872 | * 7/1999 | ............ G01N/1/20 |

* cited by examiner

*Primary Examiner*—Charles Garber
(74) *Attorney, Agent, or Firm*—White & Case LLP (57) ABSTRACT

An apparatus for use in sampling material on-line in a process system, comprising a sample collector (1) for receiving a sample of material, an elongate shaft (10) defining a passageway (14) carrying a measurement probe (11) for taking measurements from a collected sample, a pressurised fluid supply (31) connected to the passageway for delivering a pressurised fluid through the passageway to the sample collector for displacing the collected sample and a nozzle (33) provided at the distal end of the measurement probe (11) for distributing the pressurised fluid to the sample collector for displacing the collected sample from the sample collector (1).

27 Claims, 5 Drawing Sheets

SAMPLING APPARATUS

TECHNICAL FIELD OF THE INVENTION

The present invention relates to an apparatus for sampling material in a process system, in particular the on-line sampling of a flow of a liquid or powder.

BACKGROUND OF THE INVENTION

Traditionally, a sample of material would have been removed during processing from a process system and then analysed. It will be appreciated that techniques requiring the removal of material from a process system for separate analysis are both labour-intensive and time consuming.

More recently, techniques have been developed which allow material to be analysed on-line. One such device is disclosed in WO 99/32872. This document discloses a device for use in and a method of sampling material on-line in a process system which comprises a sample collector in which in use a sample of material is collected and a measuring device for taking measurements from the collected sample. The device further comprises a sample displacing means for displacing the collected sample from the sample collector so that the sample collector can receive a new sample of material. The sample displacing means comprises a pressurised gas supply, which in use is actuated to displace the collected sample and a small bore tube for leading the pressurised gas from the pressure gas source to the sample collector.

Ordinarily, this device has been found to operate satisfactorily. However, occasionally, it has been found that the sample collector is not completely emptied before receiving a new sample. Material properties of the sample, like binding forces can make it difficult to break up the sample and empty the sample collector. In some cases, sample particles have a sticky surface and tend to stick to each other or to the surface of the sample collector. It will be appreciated that even small residues of the previous sample in the sample collector are undesirable as they might influence the measurement on the next sample.

Another sampling apparatus is known from U.S. Pat. No. 5,750,996. In this document an apparatus and method for non-destructive inspection of a coated article is described. The apparatus comprises a probe, which has a recess for receiving coated article and a communicating fiberoptic receiving passageway. To displace the coated article from the recess, pressurised air is supplied to the lower portion of the recess to thereby urge the coated article out of the recess.

A drawback with the device described in U.S. Pat. No. 5,750,996 is that it is difficult to completely empty the recess of coated article. A further drawback is that the outlet for pressurised air might get clogged as particles fall down into the outlet due to its position in the bottom of the recess.

SUMMARY OF THE INVENTION

A general object of the present invention is to solve or alleviate the problems described above.

It is thus a general aim of the present invention to provide an apparatus for and a method of periodically sampling material on-line which is capable of consistently producing samples which are representative of the entire bulk of material from which samples are taken.

It is a particular aim of the present invention to provide a sampling apparatus which allows material to be sampled and replaced with new material in a quick and efficient manner.

A further aim of the present invention is to provide a sampling apparatus which ensures a stable interface between the material to be sampled and the measuring device. Where a flow of material is to be sampled, it is desirable to present a stationary sample to the measuring device.

Accordingly, the present invention provides an apparatus for use in sampling material on-line in a process system, comprising a sample collector for receiving a sample of material, an elongate shaft defining a passageway carrying a measurement probe for taking measurements from a collected sample, a pressurised fluid supply connected to the passageway for delivering a pressurised fluid through the passageway to the sample collector for displacing the collected sample, and a nozzle provided at the distal end of the measurement probe for distributing the pressurised fluid to the sample collector for displacing the collected sample from the sample collector.

In preferred embodiments the process system in which the sampling apparatus is used is a process vessel or a tubular section, such as tubes leading to or from a process vessel or bulk container.

The construction allows for a collected sample from which measurements have been taken to be replaced both simply and rapidly. The reliability in the measurements is increased as the sample collector is efficiently emptied before receiving a new sample. In addition, the configuration of the sampling apparatus of the present invention is such that it is in effect self-cleaning, thereby minimising the downtime of the process system from which material is being sampled. Moreover, the sampling apparatus of the present invention allows for the use of any kind of measuring device which utilises electromagnetic radiation.

In use the pressurised fluid supply is actuated to provide pressurised fluid to the passageway of the shaft and the nozzle through which the pressurised fluid is distributed to the sample collector to displace the collected sample. The nozzle according to the present invention decreases the risk of clogging of the displacing means, increases the number of points of action and creates a reliable functionality of the sampling apparatus.

Preferably, the nozzle is substantially ring-shaped and mounted over the distal end of the measurement probe.

Preferably, the nozzle is provided with at least one angled, spiral groove through which the pressurised fluid is distributed. In this way a turbulent and focused stream of fluid is provided to the sample collector. The angle, the size, the geometry and the number of spiral grooves all work together in creating a well defined swirl of the pressurised fluid that empties the sample collector by pneumatic transport.

Preferably, the open-topped chamber comprises an arcuate wall member on which a sample is in use collected and front wall member which is flared outwardly and upwardly.

In one embodiment the measuring device is a spectroscopic measuring device and can be a reflectance, transflectance or transmission device. Preferably, the spectroscopic measuring device is one of an emission, absorption or scattering device. In preferred embodiments the spectroscopic measuring device is an x-ray spectrophotometer, an ultra-violet (UV) spectrophotometer, a visible (VIS) spectrophotometer, an infra-red (IR) spectrophotometer, a near infra-red (NIR) spectrophotometer, a raman spectrophotometer, a microwave spectrophotometer or a nuclear magnetic resonance (NMR) spectrophotometer.

In another embodiment the measuring device is a polarimeter.

In a preferred embodiment the measuring device includes a measurement probe to be introduced into the passageway of an elongate shaft and the sample collector is attached to the distal end of the shaft. Preferably, the sample collector is releasably connected to the shaft by means of a bayonet fixing. In this way the sample collector may be easily disconnected from the shaft and the parts subject to cleaning. In another embodiment the sampling apparatus is made in one piece. Preferably, the sampling apparatus is slidably mounted through an aperture in the wall of the process vessel such as to be movable within the process system. This configuration is particularly useful when representative samples are not to be found adjacent the wall of a process system or if homogeneity is to be monitored at different locations within a process system.

Preferably, the elongate shaft is provided with an aperture through which pressurised fluid is introduced for displacement of a sample. In a preferred embodiment the pressurised fluid is a gas, for example pressurised air. In another embodiment, the pressurised fluid is a cleaning fluid that is introduced through the aperture in the shaft when the apparatus is subject to a cleaning procedure. Cleaning in place (CIP) is particular useful when cleaning the sampling apparatus between batches as the sample apparatus does not need to be removed and/or taken apart. In a still further embodiment, the fluid is a process fluid, that is a fluid used in the process carried out in the process system, i.e. a coating fluid.

In a preferred embodiment the sample collector is connected to a heating/cooling means so as to provide for temperature stabilisation of the sample collector. Temperature stabilisation can provide more reliable measurements where the measuring device is sensitive to variations in temperature or where, for example, the material to be sampled is a liquid which tends to boil and the gas bubbles generated adversely affect the measurement.

In another embodiment, at least one sensor is provided in the sample collector. For example, the sensor is a temperature sensor or a pressure sensor.

The present invention finds particular application in monitoring the characteristics of a sample of material, for example compositional changes, of pharmaceutical compositions typically in the form of powders, granules, pellets and tablets during preparation in fluidised beds. However, it will be appreciated that the present invention can equally be applied to other processes within the pharmaceutical industry, and indeed in non-pharmaceutical processes. Other processes to which the present invention can be applied are typically blender systems, powder transport devices, spray granulators, spray dryers and mixing/separation systems.

Preferred embodiments of the present invention will now be described hereinbelow by way of example only with reference to the accompanying drawings.

DESCRIPTION OF PREFERRED EMBODIMENTS

Figure 1:
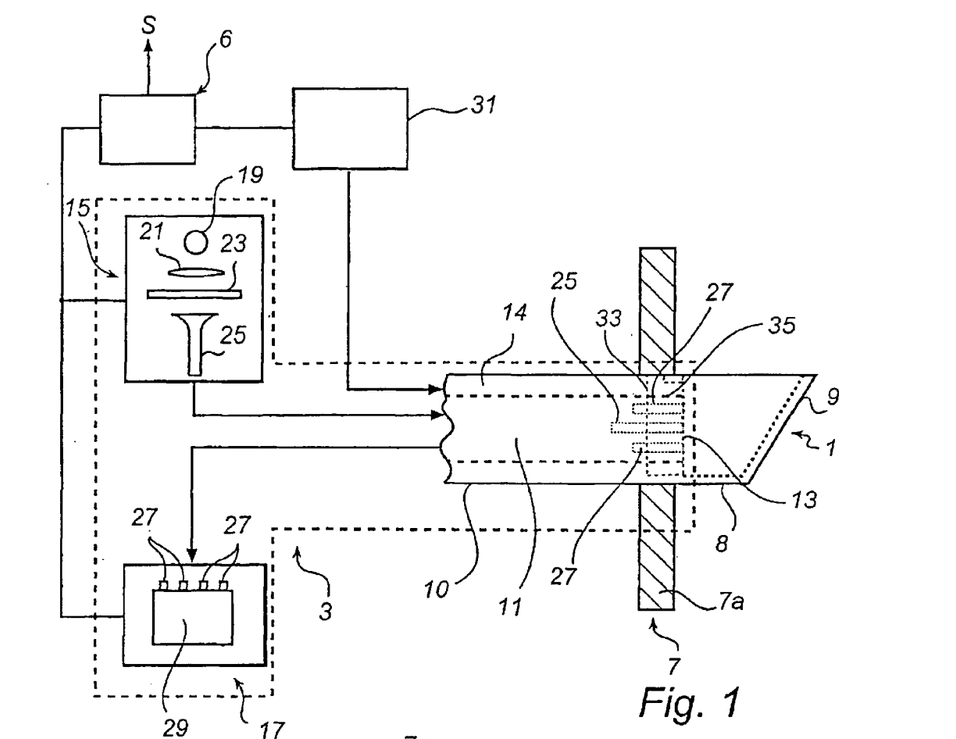
FIG. 1 schematically illustrates a sampling apparatus in accordance with a first embodiment of the present invention incorporated in a process vessel.
Figure 2:
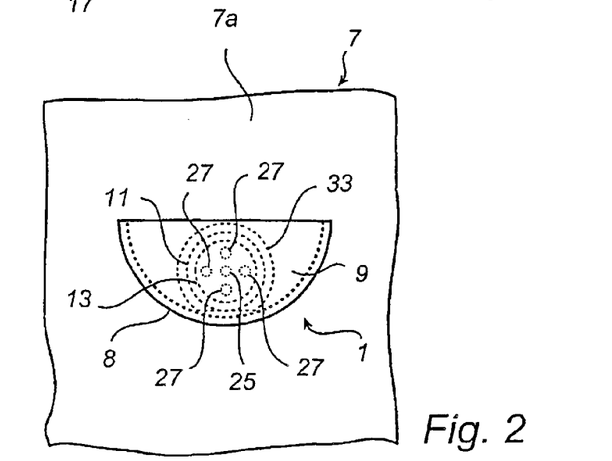
FIG. 2 illustrates a front view of the sampling apparatus of FIG. 1.
Figure 3:
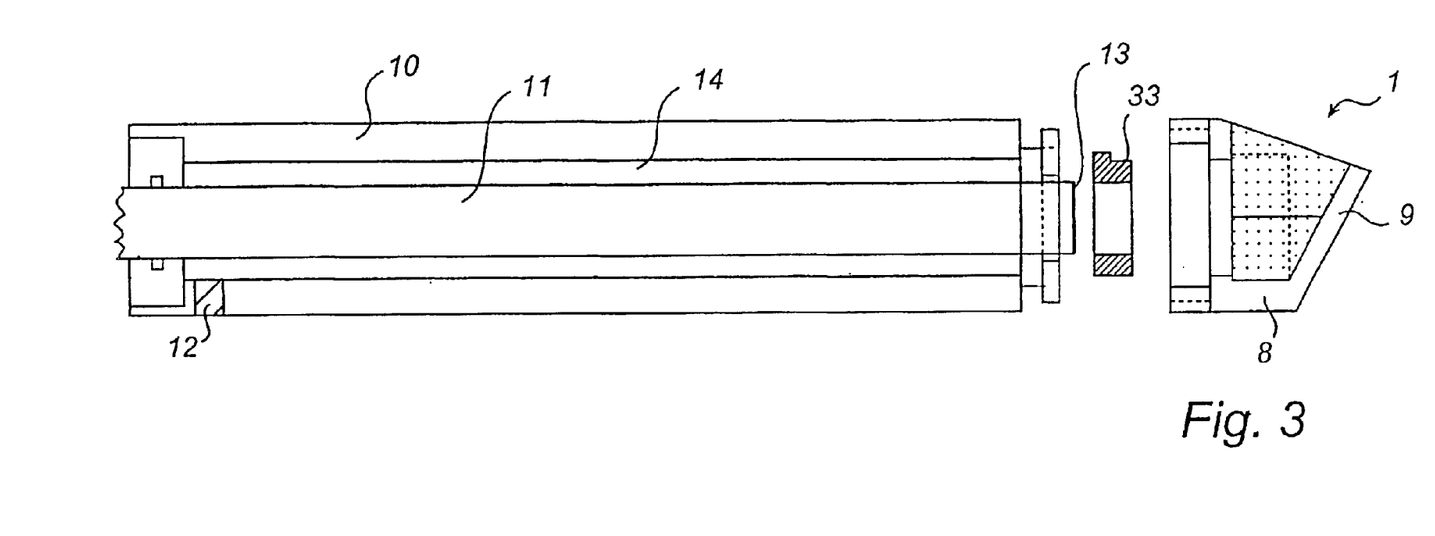
FIG. 3 illustrates an exploded view of the sampling apparatus of FIG. 1.

FIGS. 1–3 illustrate a sampling apparatus in accordance with a preferred embodiment of the present invention.

The sampling apparatus comprises a sample collector 1 for collecting a sample of material, a measuring device 3 for taking measurements from a collected sample, a sample displacement means comprising a pressurised fluid supply 31 and a nozzle 33 for distributing the supplied fluid, for displacing a collected sample and a controller 6. The operation of each of the sample collector 1, the measuring device 3 and the pressurised fluid supply is performed under the control of the controller 6, typically a computer or a programmable logic controller (PLC), as will be described in more detail hereinbelow.

The measuring device 3 includes a measurement probe 11, in this embodiment a near infra-red reflectance probe, which extends through the peripheral wall 7a of a process vessel 7 such that the distal end 13 of the measurement probe 11, through which radiation is emitted and received, is directed into the sample collector 1. In this manner measurements can be taken from a sample of material collected in the sample collector 1. The measurement probe 11 is introduced into the elongate shaft 10 connected to the sample collector 1.

The measuring device 3 further includes a radiation generating unit 15 for generating electromagnetic radiation and a detector unit 17 for detecting the radiation diffusely reflected by a collected sample.

In this embodiment the radiation generating unit 15 comprises in the following order a radiation source 19, preferably a broad spectrum visible to infra-red source, such as a tungsten-halogen lamp, which emits radiation in the near infra-red interval of from 400 to 2500 nm, a focusing lens 21, a filter arrangement 23 and at least one fibre cable 25 for leading the focused and filtered radiation to distal end 13 of the measurement probe 11. In this embodiment the filter arrangement 23 comprises a plurality of filters, each allowing the passage of radiation of a respective single frequency or frequency band. In other embodiments a monochromator or a spectrometer of Fourier transform kind can be used instead of the filter arrangement 23.

In this embodiment the detector unit 17 comprises in the following order an array of fibre cables 27, whose distal ends are arranged around the distal end of the at least one fibre cable 25 which supplies radiation to a collected sample, and a detector 29 connected to the fibre cables 27. The detector 29 is preferably an array detector such as a CMOS chip, a CCD chip or a focal plane array. The distal ends of the fibre cables 27 are preferably spaced from the distal end of the at least one fibre cable 25 in order to minimise the effect of specular reflection or stray energy reaching the fibre cables 27. In use, the detector 29 will produce signals S depending upon the composition of the sampled material and the frequency of the supplied radiation. These signals S are then amplified, filtered and digitised so as to be available for further processing. The processed signals can be used to perform real-time or subsequent analysis. Alternatively or additionally, the processed signals can be used for process control.

The sample collector 1 connected to an elongate shaft 10 is preferably slidably mounted through the peripheral wall 7a of a process vessel 7. In this way, the sample collector 1 can be positioned at a range of positions relative to the wall 7a of the process vessel 7 so as to allow measurements to be taken from samples at those positions. However, if desired, the sampling apparatus may be fixed in relation to the wall 7a at a desired position for receiving samples from a certain position in the process system.

In a preferred embodiment, the sample collector 1 defines an open-topped chamber comprising an arcuate wall member 8 on which in use powder is collected and a front wall member 9 which tapers upwardly and outwardly for assisting in guiding material thereinto. The arcuate wall member 8 defines the bottom and the sides of the open-topped chamber in the sample collector 1. Due to the arcuate shape, the emptying of the open-topped chamber is facilitated. No obstructing sharp edges are present that could hinder the sample leaving the sample collector. The upwardly and outwardly flared front wall 9 will further facilitate the emptying of the sample collector 1. Since the angle of the front wall in relation to the bottom is greater than 90 degrees, the sample can easily exit the sample collector 1 when hit by the stream of fluid from the nozzle 33.

An additional advantage of the outwardly and upwardly flared front wall 9 is that any light passing through the sample to the front wall will be reflected away instead of reflected back to the measuring device 3. Light that is reflected back to the measuring device from the front wall might disturb the measurement of the sample.

Preferably, the sample collector 1 and the elongate shaft 10 are made as two separate parts and connected before being introduced into a process vessel or the like. However, the sample collector and the elongate shaft may as well be made in one piece.

Figure 5A:
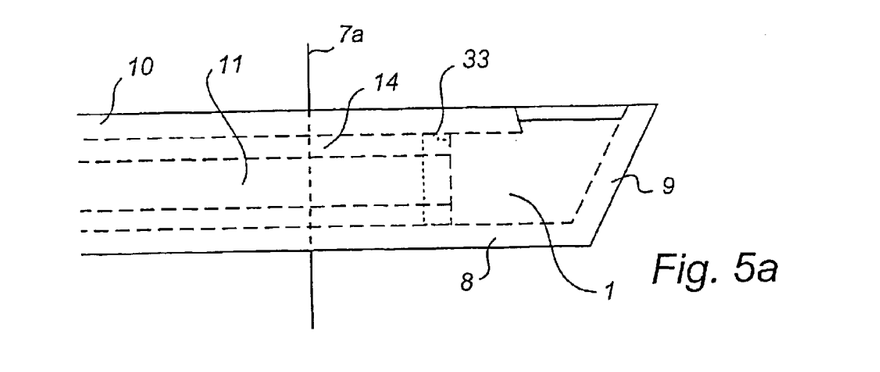
FIG. 5a schematically illustrates a sectional view of the sampling apparatus according to a second embodiment.

In another embodiment schematically illustrated in FIG. 5a the sample collector 1 consists of the open topped chamber, comprising the arcuate wall member 8 and the front wall member 9, and a portion of the distal end of the elongated shaft 10. This is achieved by not introducing the measurement probe all the way through the elongate shaft. In this way the collected sample is protected in the sample collector during the measurement while a part of the elongate shaft 10 serves as a roof over the sample received in the chamber. This embodiment is particularly useful if a sample is to be taken in a process system with turbulent conditions.

Figure 5B:
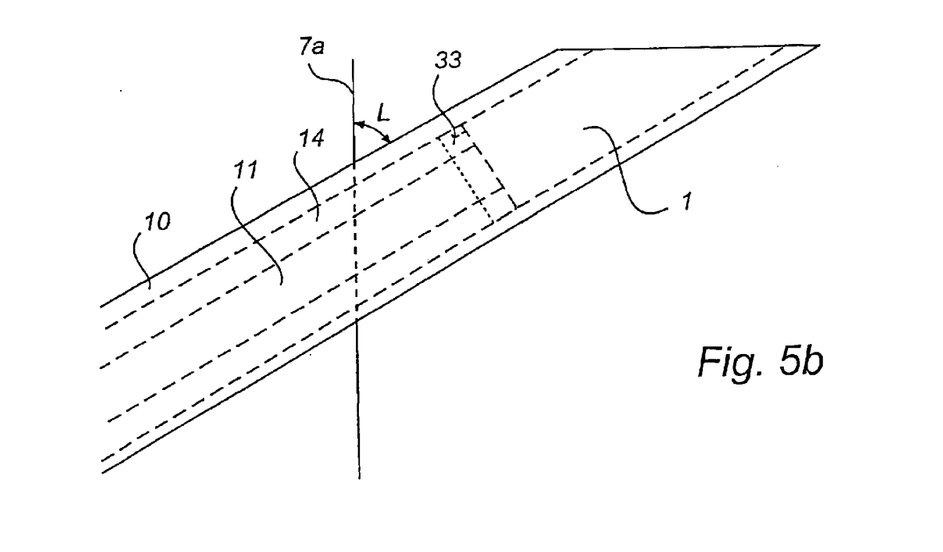
FIG. 5b schematically illustrates a sectional view of the sampling apparatus according to a third embodiment.

In a further embodiment schematically illustrated in FIG. 5b the sample collector 1 is defined in a portion of the distal end of the elongated shaft 10. In this embodiment the elongate shaft 10 is angled against the peripheral wall 7a such that bottom of the sample collector is represented by the distal end 13 of the measurement probe 11. An advantage of this embodiment is the close contact between the sample and measurement probe as the sample falls upon the distal end 13 of the measurement probe.

Figure 4A:
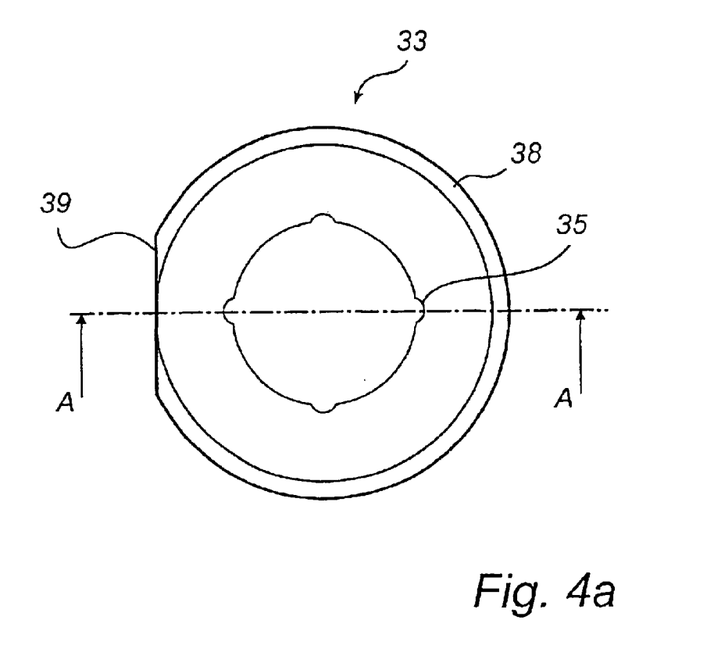
FIG. 4a illustrates a front view of the nozzle member of the sampling apparatus.
Figure 4B:
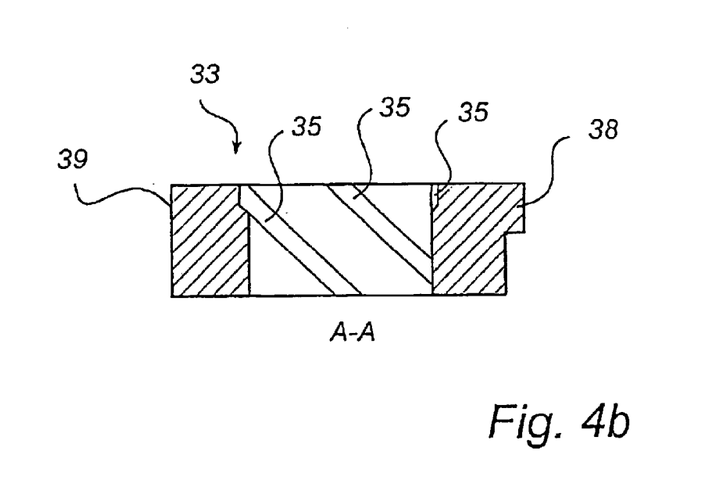
FIG. 4b illustrates a sectional view of the nozzle member of the sampling apparatus.

FIGS. 4a and 4b illustrate the nozzle 33 for distributing the pressurised fluid to the sample collector 1. The nozzle is substantially ring-shaped with a rim 38 around its outer periphery except for a smaller flat portion 39. The nozzle is held in place inside the elongate shaft 10 by the rim 38. The flat portion 39 prevents the nozzle from rotating when it is mounted in the elongate shaft 10. Preferably, the nozzle 33 is provided with one or more grooves 35 on its inner surface serving as outlets through which the pressurised liquid reaches the sample collector 1. Most preferably, the nozzle is provided with two to four grooves. However, the exact number and size of the grooves 35 depend on the particle size of the sample to be displaced. If the particle size of the sample is rather small the nozzle 33 tends to have several smaller grooves and on the other hand, if the particle size of the sample is large the nozzle should preferably have less but broader grooves. The groove 35 it self is angled in order to improve the turbulent flow creating a swirl to empty the sample collector. Preferably, the nozzle 33 is moulded from a dielectric plastics material. However, the nozzle 33 can also be made from a metal such as aluminium or stainless steel.

After a measurement has been performed, the sample is displaced by using a high-pressure fluid source 31, which in a preferred embodiment is an air compressor. The fluid source is connected to the elongate shaft 10 through an aperture 12 in the wall of the shaft. The aperture is preferably located in the proximal end of the elongated shaft 10. Pressurised fluid is provided to the nozzle 33 via the passageway 14 of the elongate shaft 10. The nozzle 33 is mounted over the measurement probe 11 and the probe is introduced into the elongate shaft. An edge cut out in the distal end of the elongate shaft will hold it in place. When high pressure fluid, in a preferred embodiment pressurised air, reaches the nozzle 33, the fluid is forced through at least one spiral groove 35 in the nozzle 33 whereby a turbulent flow, a whirl, is created in the sample collector 1 such that the sample is removed from the sample collector. Typically, the pressurised fluid is at a pressure of the order 1 bar and is supplied for about 0.1 seconds. The pressure and the duration of the pressure pulse which has to be used will vary depending upon the material being sampled.

Figure 6:
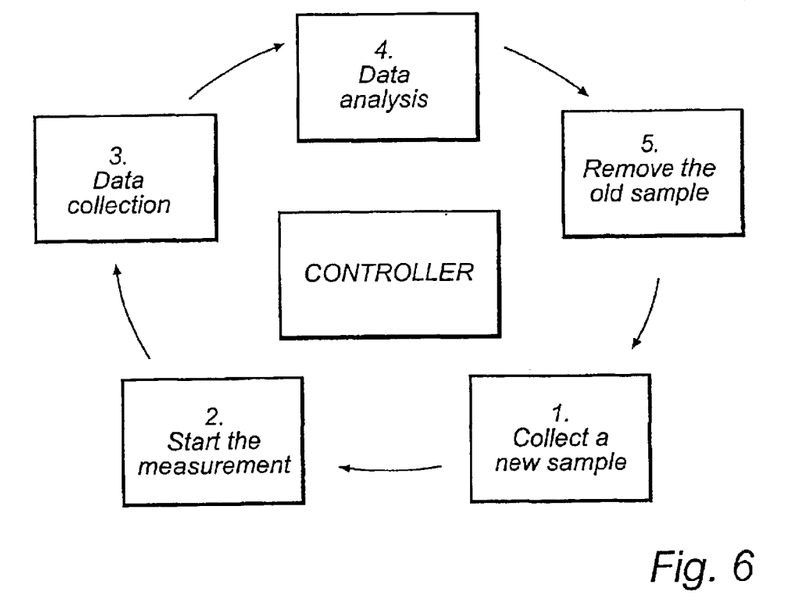
FIG. 6 illustrates a flow chart of a method of sampling material in accordance with the present invention.

The sequence of operation of the sampling apparatus 2 is schematically illustrated in FIG. 6. In use, a sample is first collected in the sample collector 1 (Step 1). The sampling apparatus is then initiated to start measurement either automatically or by the intervention of an operator (Step 2). Under the control of the controller 6, measurements are then taken from the sample collected in the sample collector 1 using the measuring device 3 to generate data corresponding to the received radiation (Step 3). As the data is generated it is then either analysed in real time or stored for subsequent analysis (Step 4), with the resulting information optionally being used for process control. After all of the required measurements have been taken from the sample, the controller 6 then actuates the sample displacement device which in this embodiment actuates the high-pressure fluid source 31, whereupon pressurised gas is delivered through the space 14 to the nozzle 33 into the sample collector 1 and the sample resident in the sample collector 1 is displaced such that a new sample can be collected (Step 5). The sampling method can then be repeated to take measurements from another sample of material.

Finally, it will be understood by a person skilled in the art that the present invention is not limited to the described embodiments but can be modified in many different ways without departing from the scope of the invention as defined in the appended claims.

What is claimed is:

1. An apparatus for use in sampling material on-line in a process system, comprising:

a sample collector for receiving a sample of material;

a measurement probe for taking measurements of the collected sample in the sample collector, wherein the measurement probe has a probe proximal and distal end;

an elongate shaft having defines a passageway for carrying the measurement probe, wherein the elongate shaft has a proximal and distal end;

a pressurised fluid supply connected to the passageway for delivering a pressurised fluid through the passageway to the sample collector for displacing the collected sample; and a nozzle provided at the distal end of the measurement probe for distributing the pressurised fluid to the sample collector for displacing the collected sample from the sample collector.

2. The apparatus according to claim 1 wherein the nozzle is substantially ring-shaped.

3. The apparatus according to claim 2 wherein the nozzle is mounted over the distal end of the measurement probe.

4. The apparatus according to claim 1, wherein the nozzle is provided with at least one spiral groove on the inner surface through which groove the pressurised fluid is distributed.

5. The apparatus according to claim 4, wherein the at least one spiral groove is angled to improve turbulence in the flow of the pressurised fluid.

6. The apparatus according to claim 1, wherein the elongate shaft is provided with an aperture in its proximal end for connection to the fluid supply.

7. The apparatus according to claim 1, wherein the sample collector is an open-topped chamber comprising an arcuate wall member on which the sample is collected.

8. The apparatus according to claim 7 wherein the sample collector comprises a front wall member which is flared upwardly and outwardly.

9. The apparatus according to claim 1 wherein the sample collector is defined by a portion of the distal end of the elongated shaft.

10. A process system comprising the apparatus according to claim 1, wherein the sample collector is located within the process system.

11. The process system according to claim 10, wherein the sample collector is movable relative to an inner surface of the process system.

12. The process system according to claim 10, further comprising a process vessel having a peripheral wall.

13. The process system according to claim 12, wherein the elongate shaft is perpendicular to the peripheral wall of the process vessel.

14. The process system according to claim 12, wherein the angle between the elongate shaft and the peripheral wall of the process vessel is less than 90°.

15. The process system according to claim 10, further comprising a tubular section.

16. The apparatus according to claim 1, wherein the measurement probe is a part of a spectroscopic measuring device.

17. The apparatus according to claim 16, wherein the spectroscopic measuring device is one of a reflectance, transflectance or transmission device.

18. The apparatus according to claim 16, wherein the spectroscopic measuring device comprises an infra-red spectrophotometer.

19. The apparatus according to claim 16, wherein the spectroscopic measuring device comprises a near infra-red spectrophotometer.

20. The apparatus according to claim 16, wherein the spectroscopic measuring device comprises an x-ray spectrophotometer.

21. The apparatus according to claim 16, wherein the spectroscopic measuring device comprises a visible spectrophotometer.

22. The apparatus according to claim 16, wherein the spectroscopic measuring device comprises a Raman spectrophotometer.

23. The apparatus according to claim 16, wherein the spectroscopic measuring device comprises a microwave spectrophotometer.

24. The apparatus according to claim 16, wherein the spectroscopic measuring device comprises a nuclear magnetic resonance spectrophotometer.

25. The apparatus according to claim 1, wherein the measurement probe is a part of a polarimeter.

26. The apparatus according to any one of claims 1 to 9 and 16–25, wherein the sample of material is a powder, a granule, a pellet, or a tablet.

27. The process system according to any one of claims 10 to 15, wherein the sample of material is a powder, a granule, a pellet, or a tablet.

* * * * *

UNITED STATES PATENT AND TRADEMARK OFFICE
CERTIFICATE OF CORRECTION

PATENT NO.       : 6,918,310 B2                                      Page 1 of 1
APPLICATION NO. : 10/466001
DATED            : July 19, 2005
INVENTOR(S)     : Björk et al.

It is certified that error appears in the above-identified patent and that said Letters Patent is hereby corrected as shown below:

Col. 6, line 63
Delete the second instance of "probe".

Col. 6, line 65
Delete "defines".

Signed and Sealed this

Twenty-ninth Day of January, 2008

JON W. DUDAS
*Director of the United States Patent and Trademark Office*